United States Patent [19]

Murata et al.

[11] 4,442,422
[45] Apr. 10, 1984

[54] HUMIDITY SENSITIVE RESISTOR

[75] Inventors: Michihiro Murata, Kyoto; Shoichi Kitao, Otokuni; Shinsei Okabe, Takatsuki, all of Japan

[73] Assignee: Murata Manufacturing Co., Ltd., Japan

[21] Appl. No.: 477,408

[22] Filed: Mar. 21, 1983

[30] Foreign Application Priority Data

Mar. 31, 1982 [JP] Japan .................................. 57-54569
Nov. 22, 1982 [JP] Japan ................................ 57-204778

[51] Int. Cl.$^3$ ............................................. H01L 7/00
[52] U.S. Cl. ........................................ 338/35; 73/73; 73/336.5; 73/27 R; 324/65 R; 338/314; 338/308; 422/98
[58] Field of Search .......................... 338/35, 34, 314; 73/336.5, 335, 29 R, 73; 324/65 R, 65 P; 340/602; 422/98; 29/610 R, 620, 613; 427/101, 102, 372 R, 376 R, 376 B

[56] References Cited

U.S. PATENT DOCUMENTS 4,167,725 9/1979 Shimizu et al. ....................... 338/35
4,263,576 4/1981 Murata et al. ....................... 338/35

FOREIGN PATENT DOCUMENTS 5145301 11/1980 Japan .................................... 338/35

*Primary Examiner*—B. A. Reynolds
*Assistant Examiner*—C. Sears
*Attorney, Agent, or Firm*—Ostrolenk, Faber, Gerb & Soffen

[57] ABSTRACT

A humidity sensitive resistor, comprising a pair of detecting electrodes (2) and (3) formed on an insulating substrate (1), and a humidity sensitive film (4) formed to coat on this detecting electrodes, the humidity sensitive film (4) being made of an integrated structure of a first layer macromolecular resin film (5) containing a polyvinyl alcohol polymer and an electrolyte and a second layer of hygroscopic macromolecular resin film (6) covering on the surface of the first layer, and humidity being detected with the aid of a change of the resistance value of this humidity sensitive film (4).

3 Claims, 11 Drawing Figures

HUMIDITY SENSITIVE RESISTOR

BACKGROUND OF THE INVENTION

1. Field of the Invention

The present invention relates to a humidity sensitive resistor wherein a change of humidity is detected as the variation of electrical resistance, and especially relates to a humidity sensitive resistor wherein a macromolecular resin film is used as a humidity sensitive film.

2. Description of the Prior Art

Hitherto humidity sensitive resistors are known such as a so-called Dunmore type humidity sensitive resistor wherein electrolytes, for example, lithium chloride (LiCl) are coated on the surface of the insulating substrate, a humidity sensitive resistor which is composed of an organic macromolecular electrolyte film, and so on.

In the conventional humidity sensitive resistor, the impedance between detecting electrodes changes by means of ionization of lithium chloride due to moisture absorption. The latter humidity sensitive resistor takes advantage of the hygroscopic property and ionconductivity of the macromolecular electrolyte film, and the impedance between detecting electrodes changes in the same manner. However, since all humidity sensitive resistors have hydrophilic character, these humidity sensitive resistors are dissolved owing to absorption of water in high humidity or dew fall condition, so that these humidity sensitive resistors suffer the disadvantage such as the poor water resisting property and lack of operation stability. For improving these disadvantages, an attempt to cross-link a film composed of hydrophilic polymer or macromolecular electrolyte can be considered. But, on the contrary, a drop of responsibility is caused when humidity sensitive resistors possess the water resisting property with the aid of cross-linked structure, so that a lowering of the detection characteristic is produced. Therefore, this is not considered as a preferred solution of the problem.

SUMMARY OF THE INVENTION

Accordingly, a principal object of this invention is to afford a humidity sensitive resistor that has an excellent water resisting property, that is, the excellent operation stability without impairment of the humidity detective characteristic.

In brief, this invention is a humidity sensitive resistor comprising a pair of detecting electrodes formed on the insulating substrate and a humidity sensitive film formed by coating on the detecting electrodes, wherein the humidity sensitive film is formed of an integrated structure of a first layer macromolecular resin film including a polyvinyl alcohol polymer and an electrolyte and a second layer of hygroscopic macromolecular resin film coating on the first layer macromolecular resin film, and the water absorbing rate of the second layer macromolecular resin film being smaller than that of the first layer macromolecular resin film.

In the other aspect of this invention, the first layer macromolecular resin film further comprises a cellulose derivative beside a polyvinyl alcohol polymer and an electrolyte. Moreover, it is preferable that the second layer macromolecular resin film comprises at least one member of a polyalkyl alcohol polymer and a cellulose derivative.

These and other features and objects of this invention will become more apparent from the following detailed description to be given with reference to the drawings.

These objects and other objects, features, aspects, and advantages of the present invention will be more apparent from the following detailed description of the present invention when taken in conjunction with the accompanying drawings.

DETAILED DESCRIPTION OF THE INVENTION

Figure 1:
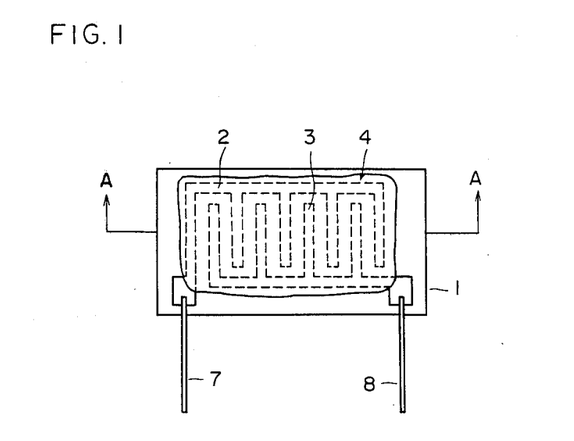
FIG. 1 is a plan view showing one example of the structure of a humidity sensitive resistor of this invention.
Figure 2:
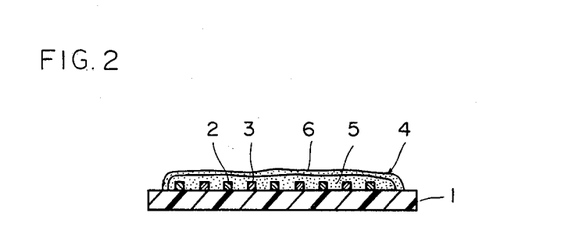
FIG. 2 is a sectional view taken along the line A—A in FIG. 1.

FIG. 1 is a plan view showing one example of the structure of the humidity sensitive resistor of the present invention, and FIG. 2 is a sectional view taken along the line A—A in FIG. 1. Referring to FIG. 1 and FIG. 2, the detecting electrodes 2 and 3 are formed on the insulating substrate 1 composed of any alumina, zirconia, etc. It should be pointed out that the forms of the detecting electrodes 2 and 3 are not restricted to the form illustrated in FIGS. 1 and 2. The humidity sensitive film 4 is formed by coating on the detecting electrodes 2 and 3. As is clear from FIG. 2, the humidity sensitive film 4 is composed of the integrated structure of the first layer macromolecular resin film 5 and the second layer macromolecular resin film 6 coating on the surface of the first layer. Further, 7 and 8 are the lead wires, which are led out from the detecting electrodes 2 and 3. In the humidity sensitive resistor of the present invention, the humidity in atmospheres to be detected is determined by measuring the change of resistance values between the detecting eletrodes 2 and 3.

Embodiment 1

In a preferred embodiment of the present invention, the first layer macromolecular resin film 5 comprises a polyvinyl alcohol polymer and an electrolyte. Further, the second layer macromolecular resin film 6 has a characteristic that its water absorbing rate is smaller than that of the first layer macromolecular resin film 5.

Polyvinyl alcohol polymers which can be employed in this embodiment are as follows.

(1) Vinyl acetate and other various kinds of vinyl ester polymers, and products obtained by completely or partly saponification of these copolymers.

(2) Saponified copolymer products copolymerized of vinyl acetate or other various kinds of vinyl esters and various kinds of unsaturated monomers such as α-olefins, vinyl chloride, acrylonitrile, acrylamide acrylic acid esters, and methacrylic acid esters.

(3) Polyvinyl alcohol copolymers esterified with cyclic acid anhydride of polyvinyl alcohol polymers described above and polyvinyl alcohol polymers denaturated with carboxyl groups.

"Electrolytes" are substances which give ion-conductivity by moisture absorption, and both inorganic and organic electrolytes can be utilized. For example, alkali or alkaline earth salts are known as inorganic electrolytes, and organic electrolytes include, e.g., (a) organic acid salts such as sodium acetate, sodium acrylate, and the like, (b) macromolecular organic acids and their salts such as sodium polyacrylate, sodium polyglutarate, and the like, (c) alkyl-sulfonic acid and its alkali, ammonium, and amine salts, and (d) arylsulfonic acid and its alkali, ammonium, and amine salts.

As the hygroscopic high molecular resin film constituting the second layer, the followings are given.

(1) Cellulose derivatives such as diacetyl cellulose, methyl cellulose, ethyl cellulose, hydroxyethyl cellulose, carboxymethyl cellulose, cyanoethyl cellulose, and the like.

(2) Various kinds of polyvinyl alcohol polymers such as polyvinyl acetate, polyvinyl chloride, polymethyl vinyl ketone, polyvinyl isobutyl ether, and the like.

(3) Polyalkyl alcohol polymers such as polybutyl alcohol, polymethyl aryl alcohol, and the like.

(4) Polyacryl polymers such as hydroxyalkyl acrylate, partly esterified products of polyalkyl acrylic acid, polymethyl methacrylate, and the like.

(5) Acrylonitrile (6) Epoxy Polymer

The water absorbing rate of polyvinyl alcohol used for the first layer macromolecular film and the typical material used for the second layer macromolecular films are shown in Table 1.

TABLE 1

| | material | water absorbing rate at the relative humidity of 80% |
|---|---|---|
| first layer | polyvinyl alcohol polymer | 20–80% |
| | ethyl cellulose | 2.6% |
| | polyvinyl acetate | 3.4% |
| | polyvinyl chloride | 0.8% |
| | polyvinyl methyl ketone | 2.9% |
| second layer | polyvinyl isobutyl ether | 0.5% |
| | polymethyl aryl alcohol | 5.7% |
| | polymethyl methacrylate | 1.4% |
| | polyacrylonitrile | 1.8% |
| | epoxy polymer | <0.1% |

The humidity sensitive resistor of this embodiment having the constitution described above brings about the following effects.

The first layer macromolecular resin film consists of a polyvinyl alcohol polymer and an electrolyte. However, it is not homogeneous from the viewpoint of the structure, and take the structure wherein partially crystalized microfibrous granular parts of polyvinyl alcohol polymers exist through the noncrystal parts. Consequently, in the first layer, microchannel of noncrystal parts is formed in the grain boundaries of the fibrous granular parts. On the other hand, many of the electrolyte exist mainly in these noncrystal parts, and it is estimated that ionconduction accompanied with the moisture absorption is achieved through this microchannel. Although the impedance between the electrodes changes due to the relative humidity in the case of this first layer alone, the electrolyte is dissolved and the impedance between the electrodes increases immediately if a drop of water adheres to the surface, so that this first layer cannot be utilized as a humidity sensitive resistor. However, from this embodiment, the integrated structure is made by forming the second layer macromolecular resin film on such the first layer macromolecular resin film, and the water absorbing rate of the second layer macromolecular resin film by moisture absorption is smaller than that of the first layer macromolecular resin film, wherein the disadvantages described above can be improved. That is to say, the second layer macromolecular resin film can obtain large area for junction based upon the bumpy surface due to the fibrous granular parts of the first layer macromolecular resin film, and sturdy junction state is realized. It was proved that, in such integrated structure, the elution amount of the electrolyte contained in the first layer macromolecular resin film into water could be depressed to a negligibly small degree and the variation of the impedance between the electrodes did not take place at all if the water absorbing rate of the second layer macromolecular resin film by moisture absorption was made to be smaller than that of the first layer macromolecular resin film. As a matter of course, it goes without saying that the control of the respective film thickness of the first layer macromolecular resin film and the second layer macromolecular resin film constituting the humidity sensitive resistor is needed in order to gain a fixed characteristic because responsibility and sensitivity change according to each film thickness. Besides, in the humidity sensitive resistor relating to this invention, the relative humidity-resistance value characteristic can be changed by altering the concentration of the electrolyte. By the way, in the low concentration of the electrolyte, the humidity sensitive resistor being useful as a humidity switching element of which the resistance value changes steeply in high humidity can be obtained. Further, the swelling degree can be changed by changing the degree of saponification of polyvinyl alcohol polymers, so that adjustment of the humidity sensitive characteristic becomes feasible. Glass transition point can be changed by changing the degree of polymerization of polyvinyl alcohol polymers and the like. A temperature characteristic of the humidity sensitive resistor can be altered by changing the glass transition point, and consequently utilization of this characteristic can serve the humidity sensitive resistor to be adjusted in the usable temperature range, so that polyvinyl alcohol polymers, use of which was so far believed difficult, can be applied to practical use as a humidity sensitive resistor. As mentioned above, owing to the layer integrated structure of the humidity sensitive film, remarkable improvement of the water resisting property, which is difficult in the case of the humidity sensitive resistor composed of conventional hydrophilic macromolecular resin, can be realized.

Next, specific experimental examples in the first embodiment described above will be explained as follows.

EXAMPLE 1

An alumina substrate was prepared as an insulating substrate, and combtooth-shape gold electrodes which have 300 μm of interval between electrodes and 48 mm of the length of opposing electrodes were formed on the alumina substrate as detecting electrodes. Then, each paste constituting the first layer macromolecular resin film of which composition was shown in Table 2 was smeared on the almina substrate in such a way to coat the detecting electrodes, and this smeared film was dried. After that, each paste constituting the second layer macromolecular resin film as also shown in Table 2 was smeared in such a way to coat the first layer macromolecular resin film described above, and then this smeared film was treated by heating at 150° C.

Figure 3:
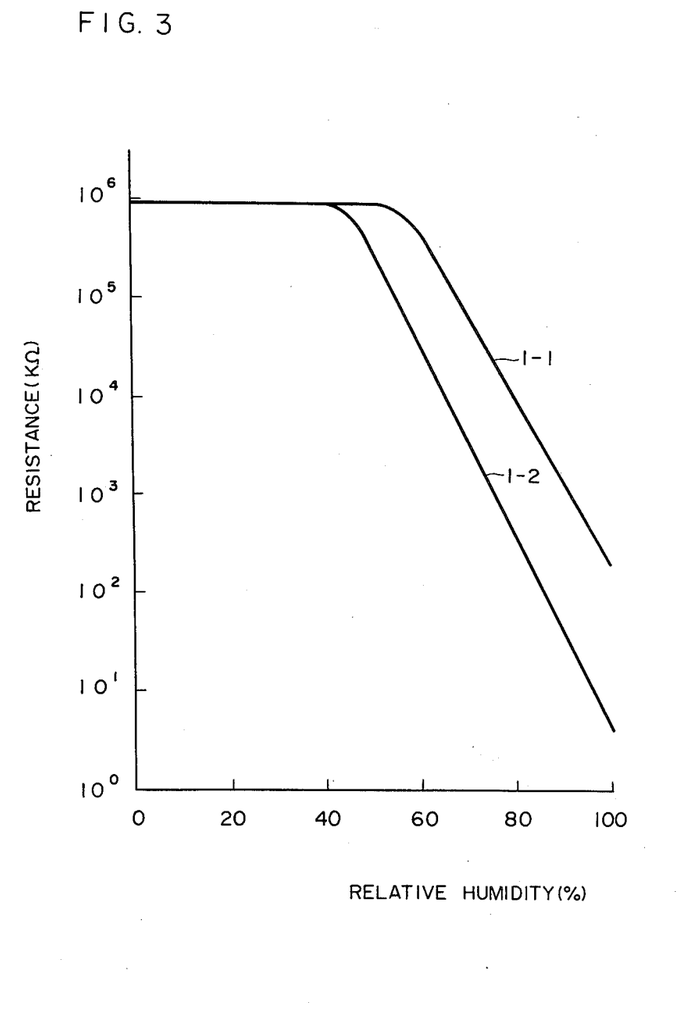
FIG. 3 through FIG. 7 are graphs showing a relative humidity-resistance characteristic obtained by the first embodiment of this invention.
Figure 4:
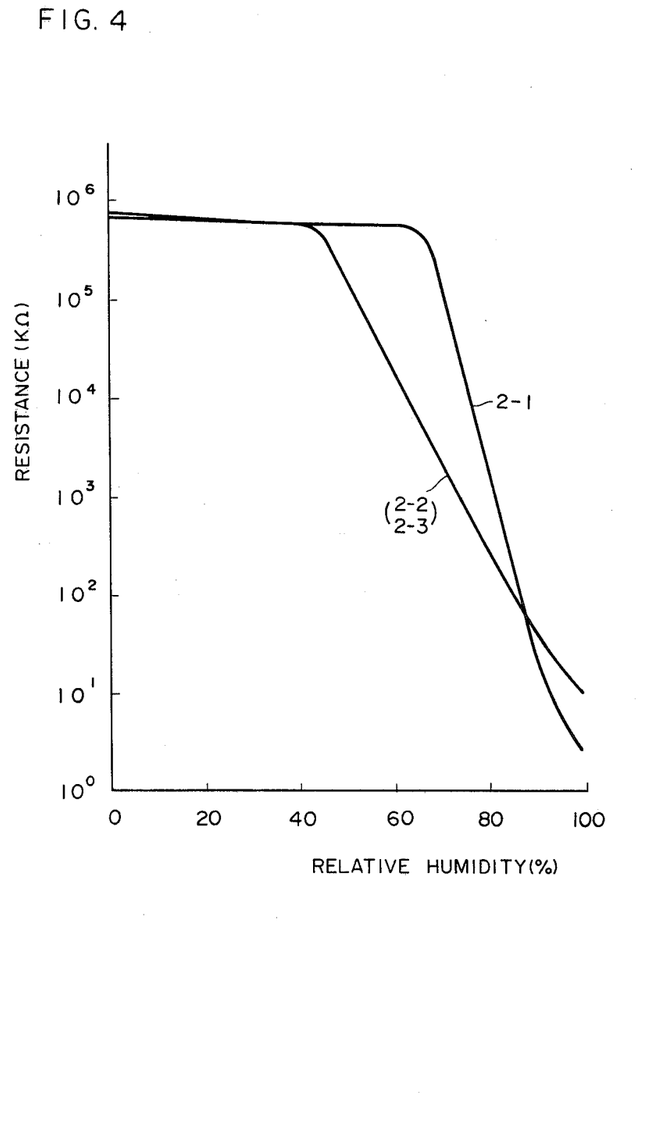
Figure 5:
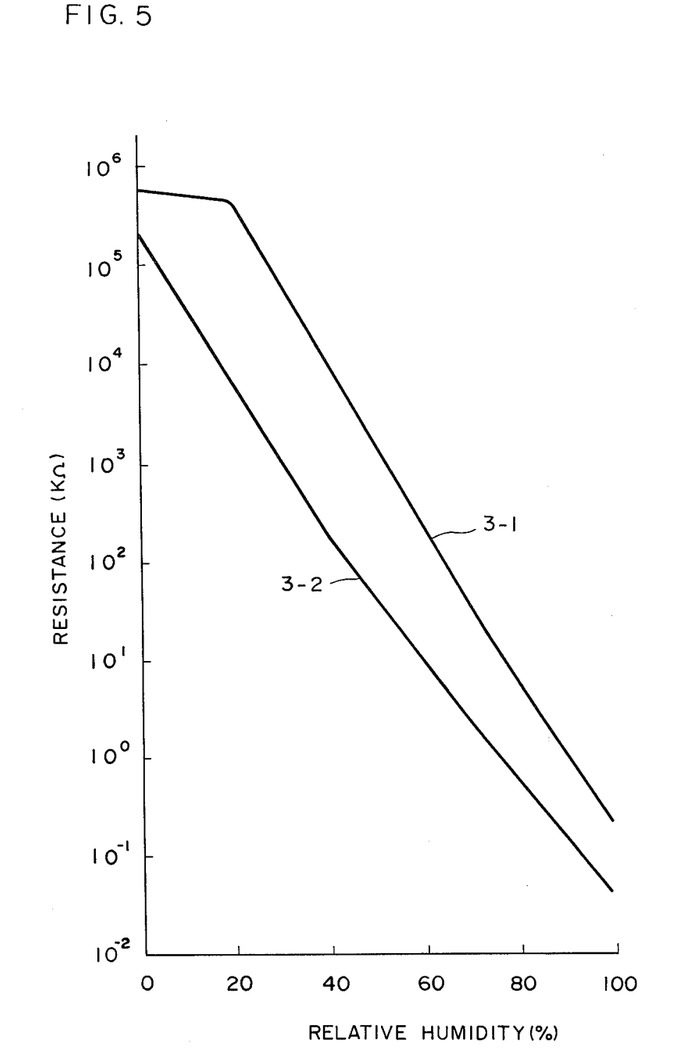
Figure 6:
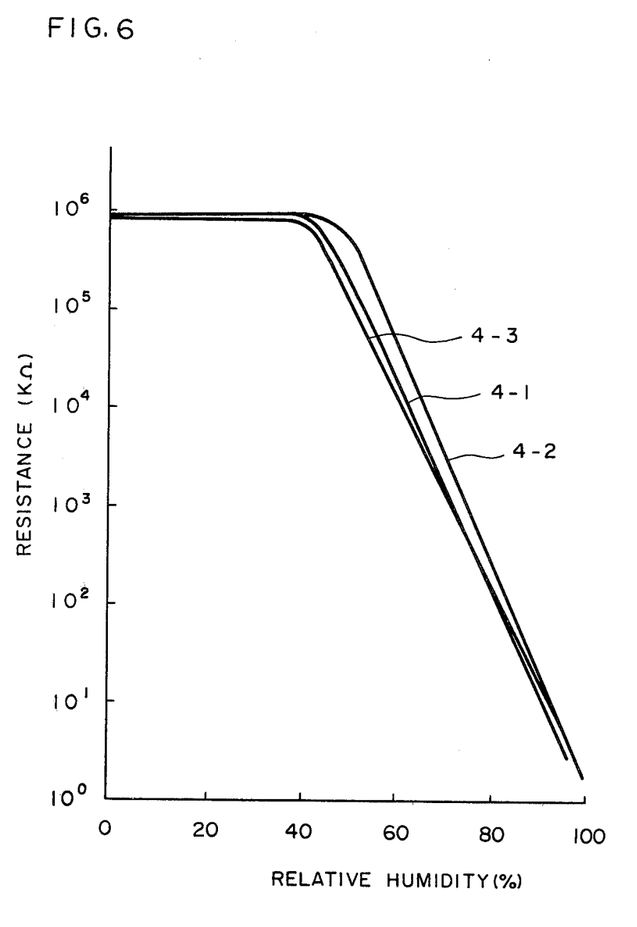
Figure 7:
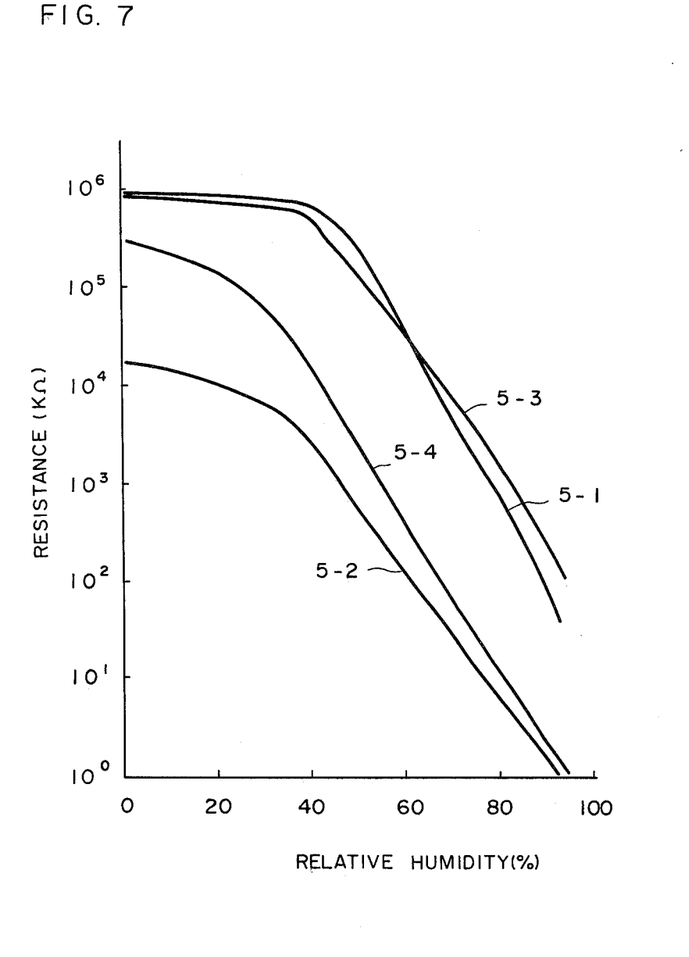

Further, each humidity sensitive resistor was obtained by attaching the lead wires to the detecting electrodes. The relative humidity-resistance value characteristic of each humidity sensitive resistor produced as described above was determined, and then the results shown in FIG. 3 through FIG. 7 were gained. FIG. 3 shows the characteristics of sample 1-1 and sample 1-2, and FIG. 4 shows the characteristics of sample 2-1, sample 2-2, and sample 2-3. FIG. 5 shows the characteristics of sample 3-1 and sample 3-2, and FIG. 6 shows the characteristics of sample 4-1, sample 4-2, and sample 4-3. FIG. 7 shows the characteristics of sample 5-1, sample 5-2, sample 5-3, and sample 5-4. Moreover, it is pointed out that the numbers in each drawing agrees with the sample numbers shown in Table 2.

TABLE 2

| sample number | first layer macromolecular resin film | | | second layer macromolecular resin film | |
|---|---|---|---|---|---|
| | polyvinyl alcohol polymer | electrolyte | solvent | kind of resin | solvent |
| 1-1 | polyvinyl alcohol (10 g) | sodium acetate (0.5 %) | 80% alcohol aqueous solution (100 ml) | ethyl cellulose (2 g) | alcohol (100 ml) |
| 1-2 | polyvinyl alcohol (10 g) | sodium acetate (1.0 %) | 80% alcohol aqueous solution (100 ml) | ethyl cellulose (2 g) | alcohol (100 ml) |
| 2-1 | maleic acid denaturated polyvinyl alcohol (maleic acid:PVA = 1:9) (10 g) | sodium acetate (0.5 %) | 80% alcohol aqueous solution (100 ml) | ethyl cellulose (2 g) | alcohol (100 ml) |
| 2-2 | acryl-denaturated polyvinyl alcohol (acryl:PVA = 1:1) (10 g) | sodium acetate (0.5%) | 80% alcohol aqueous solution (100 ml) | ethyl cellulose (2 g) | alcohol (100 ml) |
| 2-3 | acryl-denaturated polyvinyl alcohol (acryl:PVA = 7:3) (10 g) | sodium acetate (0.5 %) | 80% alcohol aqueous solution (100 ml) | ethyl cellulose (2 g) | alcohol (100 ml) |
| 3-1 | acryl-denaturated polyvinyl alcohol (acryl:PVA = 1:1) (10 g) | soduim acetate (1.0 %) | 80% alcohol aqueous solution (100 ml) | ethyl cellulose (2 g) | alcohol (100 ml) |
| 3-2 | acryl-denaturated polyvinyl alcohol (acryl:PVA = 1:1) (10 g) | sodium acetate (2.5 %) | 80% alcohol aqueous solution (100 ml) | ethyl cellulose (2 g) | alcohol (100 ml) |
| 4-1 | acryl-denaturated polyvinyl alcohol (acryl:PVA = 1:1) (10 g) | sodium acetate (0.5 %) | 80% alcohol aqueous solution (100 ml) | polybutyl alcohol (2 g) | acetone (100 ml) |
| 4-2 | acryl-denaturated polyvinyl alcohol (acryl:PVA = 1:1) (10 g) | sodium acetate (0.5 %) | 80% alcohol aqueous solution (100 ml) | Polymethacrylic acid ester (65% esterification) (2 g) | acetic acid (100 ml) |
| 4-3 | acryl-denaturated polyvinyl alcohol (acryl:PVA = 1:1) (10 g) | sodium acetate (0.5%) | 80% alcohol aqueous solu- | epoxy resin (2 g) | butyl cellosolve (100 ml) |
| 5-1 | polyvinyl alcohol (10 g) | sodium polyacrylate (0.5%) | 80% alcohol aqueous solution (100 ml) | ethyl cellulose (2 g) | alcohol (100 ml) |
| 5-2 | polyvinyl alcohol (10 g) | lithium acetate (1%) | 80% alcohol aqueous solution (100 ml) | ethyl cellulose (2 g) | alcohol (100 ml) |
| 5-3 | polyvinyl alcohol (10 g) | cesium acetate (1%) | 80% alcohol aqueous solution (100 ml) | ethyl cellulose (2 g) | alcohol (100 ml) |
| 5-4 | polyvinyl alcohol (10 g) | rubidium acetate (4%) | 80% alcohol aqueous solution (100 ml) | ethyl cellulose (2 g) | alcohol (100 ml) |

As can be seen from FIG. 3, from the results of each experimental example about the humidity sensitive resistor of this embodiment, the humidity sensitive resistor, having the characteristic that the resistance value rapidly drops in high humidity and also having the switching characteristic at particular humidity, can be obtained. FIG. 4 shows that the switching characteristic can be altered by changing the kind of polyvinyl alcohol polymers. Further, from FIG. 5, it is comprehensible that the characteristic can be changed by varying concentration of the electrolyte.

FIG. 6 is a graph showing the characteristic of the humidity sensitive resistor composed of the different kind of the second layer macromolecular resin film coating on the first layer macromolecular resin film.

It is understandable that a remarkable change of the characteristic does not yield even if the different kind of the second layer macromolecular resin film is employed granting that the first layer macromolecular resin film is identical. FIG. 7 shows that the characteristic of the humidity sensitive resistor in this embodiment can be changed with the aid of altering the kind of the electrolyte.

EXAMPLE 2

Next, a cycle try of dipping in water for 30 seconds and drying for 10 minutes was repeated 1000 times for each humidity sensitive resistor obtained in the Example 1 of the first embodiment described above, and then the resistance value was determined in 90% relative humidity. The result thus obtained is shown in Table 3. In addition, the initial resistance value in 90% relative humidity is shown together in Table 3.

TABLE 3

| sample number | initial resistance value | resistance value after 1000 cycles |
|---|---|---|
| 1-1 | 1.4 M Ω | 1.9 M Ω |
| 1-2 | 40 K Ω | 80 K Ω |
| 2-1 | 23 K Ω | 55 K Ω |
| 2-2 | 45 K Ω | 56 K Ω |
| 2-3 | 45 K Ω | 60 K Ω |
| 3-1 | 1.1 K Ω | 1.3 K Ω |
| 3-2 | 160 Ω | 240 Ω |
| 4-1 | 10 K Ω | 12 K Ω |
| 4-2 | 17 K Ω | 80 K Ω |
| 4-3 | 11 K Ω | 21 K Ω |
| 5-1 | 100 K Ω | 130 K Ω |
| 5-2 | 1.6 K Ω | 3.5 K Ω |
| 5-3 | 320 K Ω | 400 K Ω |
| 5-4 | 2.5 K Ω | 3.3 K Ω |

Figure 8:
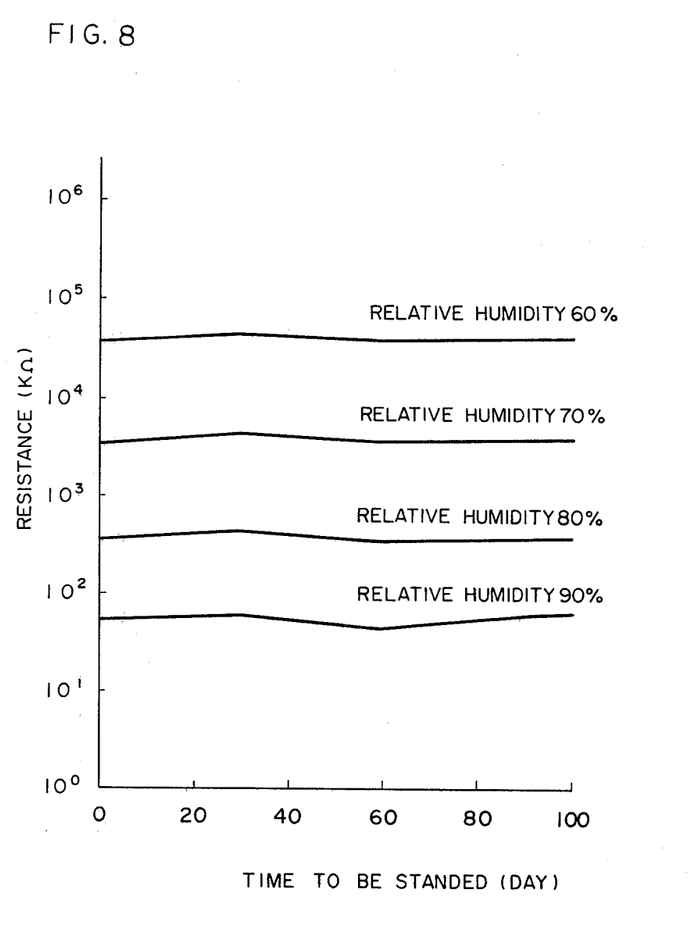
FIG. 8 is a graph showing of a change of resistance value with the elapse of time of the first embodiment of the present invention.

As is clear from Table 3, the humidity sensitive resistor of this embodiment is proved to have the characteristic that a change of the resistance value is small, and to be excellent in water resisting property. As a comparative Example 1, the similar experiment was achieved for a humidity sensitive resistor which did not form a surface layer composed of a macromolecular resin film, wherein the resistance value increased more than one order even after only one cycle experiment, and extremely remarkable deterioration of the characteristic was seen. Further, in sample 2-2, temperature effect of the humidity-resistance value characteristic was determined by using acryldenaturated polyvinyl alcohols of which glass transition points were 20° C. and 50° C., respectively, and temperature variation ratios of the relative humidity-resistance value characteristic were 1% RH/°C. and 0.5% RH/°C., respectively. As is evident from this experiment, the humidity sensitive resistor of this embodiment is proved to have the characteristic that the relative humidity-resistance value changes on a small scale against temperature variation. By using the humidity sensitive resistor of sample 2-2, the humidity sensitive resistor was set up in each condition that the relative humidity was 60%, 70%, 80%, and 90%, respectively, and then the resistance values after about 3 months were determined. The result thus obtained is shown in FIG. 8. As is clear from FIG. 8, changes of resistance values were scarcely observed even in the case that the humidity sensitive resistor was set under settled humidity conditions, and it is understandable that the humidity sensitive resistor possesses stable humidity detection characteristic.

EXAMPLE 3

As is clear from the explanation of the first embodiment of this invention described above, a humidity sensitive resistor having an excellent water resisting property can be obtained in such a way that a humidity sensitive film takes an integrated structure of a first layer macromolecular resin film containing a polyvinyl alcohol polymer and an electrolyte and a second layer of hygroscopic macromolecular resin film coating on the first layer macromolecular resin film. However, from the repetition of a number of various kinds of experiments by the present inventor, it is proved that a humidity sensitive film is formed of an integrated structure of the first layer macromolecular resin film containing a polyvinyl alcohol polymer, a cellulose derivative, and an electrolyte and the second layer macromolecular resin film coated on the surface of the first layer comprising at least one member of a polyalkyl alcohol polymer and a cellulose derivative, wherein a humidity sensitive resistor having a more excellent water resisting property, namely a more excellent operation stability, can be obtained. In the following, the second embodiment of this invention having such a constitution will be explained.

As described above, in the second embodiment of this invention, the first layer resin film is composed of a polyvinyl alcohol polymer, a cellulose derivative, and an electrolyte. Polyvinyl alcohol polymers and electrolytes are the same as that of being usable in the first embodiment described above. Methyl cellulose, ethyl cellulose, diacetyl cellulose, hydroxyethyl cellulose, carboxymethyl cellulose, cyanoethyl cellulose, and the like can be used as "cellulose derivatives".

Besides, the same cellulose derivatives in the first layer described above can be used as cellulose derivatives constituting the second layer macromolecular resin film. Further, polybutyl alcohol, polymethyl alcohol, and the like can be utilized as "polyalkyl alcohol polymers" forming the second layer macromolecular resin film.

As is clear from Example 3 as will be described later, it is enough that the second layer macromolecular resin film contains at least one member of a polyalkyl alcohol polymer and a cellulose derivative, and it may or may not contain both.

Since preparation of the humidity sensitive resistor in the second embodiment is made in the same procedure as that of the first embodiment, the explanation is omitted. In brief, the characteristic in the second embodiment is at the point that the first layer macromolecular resin film further includes "a cellulose derivative". Experimental example about the humidity sensitive resistor in the second embodiment possessing such composition will be explained below.

EXAMPLE 4

An alumina substrate was prepared as an insulating substrate, the gold combtooth-shape detecting electrodes, which have 30 μm of interval between electrodes and 48 mm of the length of the opposing electrodes, were formed on this alumina substrate. Next, each paste, which constitutes the first layer macromolecular resin film having the composition shown in Table 4 was smeared on the alumina substrate to coat the detecting electrodes and was dried. After drying, each paste, which constitutes the second layer macromolecular resin film having the composition also shown in Table 4, was smeared to coat the first layer macromolecular resin film, and was treated by heating at 150° C. Further, each humidity sensitive resistor was obtained by attaching the lead wires to the detecting electrodes. Besides, comparative Example 2 was obtained in the similar manner as each sample described above by using the first layer macromolecular resin film which is free from cellulose derivatives.

ple 6-1 and sample 6-2 in this embodiment are proved to have an extremely excellent water resisting property compared with comparative Example 2. From FIG. 7, it is also understandable that the water resisting property can be changed by altering the kind and concentration of the electrolyte.

EXAMPLE 4

Each humidity sensitive resistor in the second embodiment was gained in the similar manner as with the case of Example 2 by using the material of macromolec-

TABLE 4

| sample number | first layer macromolecular resin film | | | | second layer macromolecular resin film | |
|---|---|---|---|---|---|---|
| | polyvinyl alcohol polymer | cellulose derivation | electrolyte | solvent | kind of resin | solvent |
| comparative example 2 | polyvinyl alcohol (100%) | — | sodium acetate (1.0%) | 80% alcohol aqueous solution (100 ml) | ethyl cellulose (2 g) | 100% alcohol aqueous solution (100 ml) |
| sample 6-1 | polyvinyl alcohol (50%) | ethyl cellulose (50%) | sodium acetate (1.0%) | 80% alcohol aqueous solution (100 ml) | ethyl cellulose (2 g) | 100% alcohol aqueous solution (100 ml) |
| sample 6-2 | polyvinyl alcohol (50%) | ethyl cellulose (50%) | toluenesulfonic acid triethanol amine salt (50%) | 80% aqueous aqueous solution (100 ml) | ethyl cellulose (2 g) | 100% alcohol aqueous solution (100 ml) |

Figure 9:
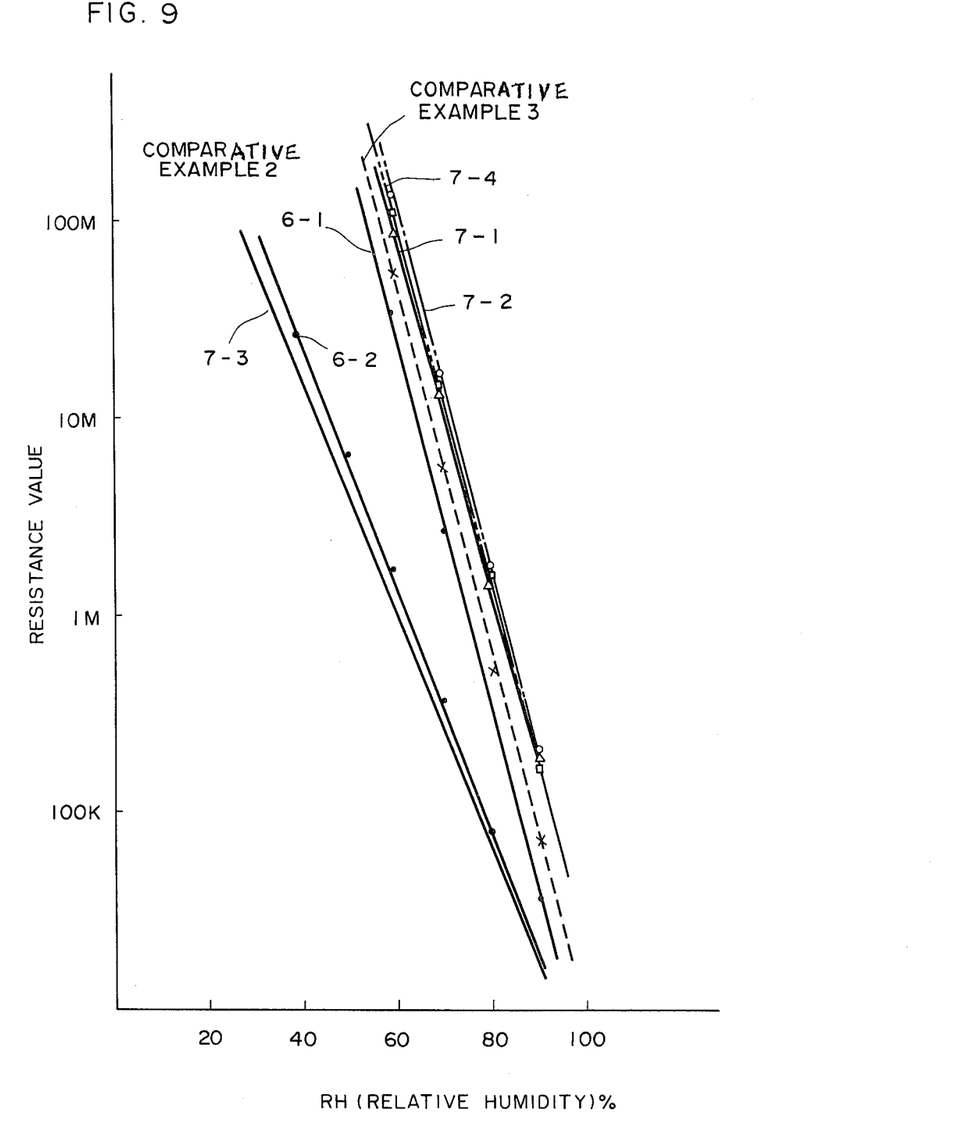
FIG. 9 is a graph showing the resistance value in the relative humidity of each experimental example in the second embodiment of the present invention.
Figure 10:
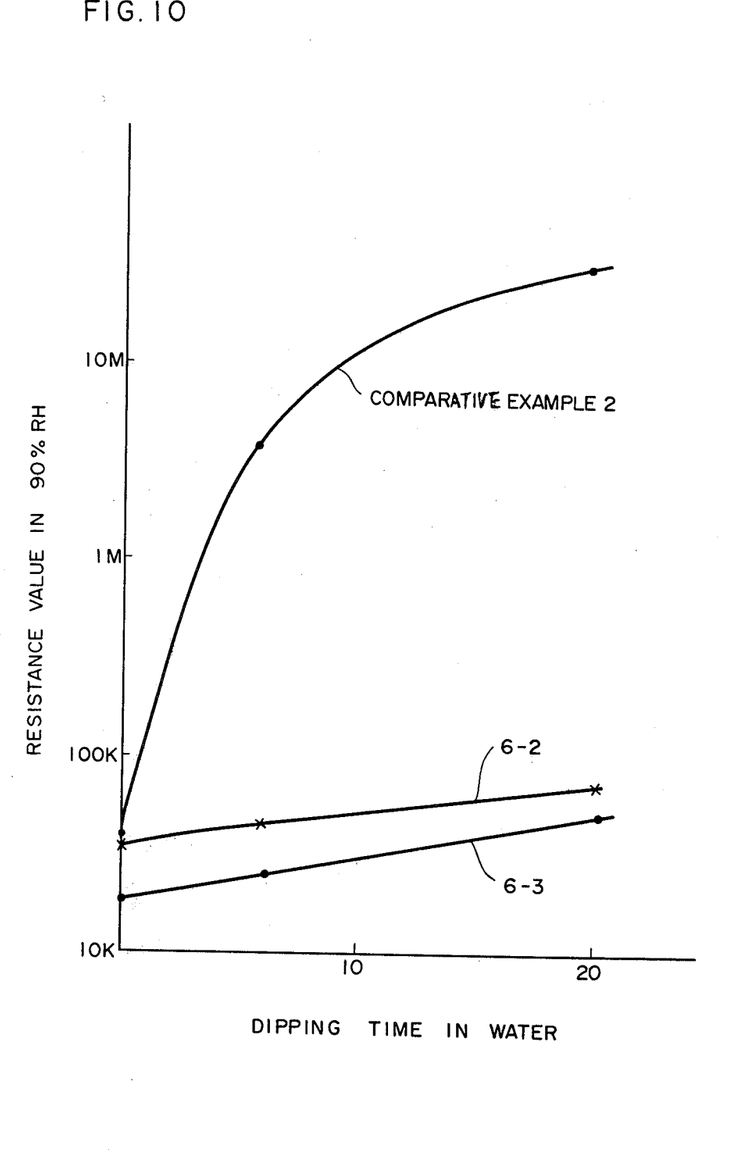
FIG. 10 is a graph showing the resistance value in 90% relative humidity of the experimental Example 1 of the second embodiment.

For comparative Example 2, sample 6-1, and sample 6-2, respectively, the resistance value in each relative humidity was determined with the aid of 1 volt of applied alternating current voltage. The result thus obtained is shown in FIG. 9. Furthermore, after comparative Example 2 and each sample were dipped and permitted to stand for a fixed time, they were pulled up from the water and dried, and the resistance value in 90% relative humidity was determined. The result is shown in FIG. 10. As is clear from FIG. 10, both samular resin film consisting of the composition shown in Table 5. As a comparative Example 3, a humidity sensitive resistor, of which a first layer macromolecular resin film did not contain a cellulose derivative, was prepared.

TABLE 5

| sample number | first layer macromolecular resin film | | | | second layer macromolecular resin film | |
|---|---|---|---|---|---|---|
| | polyvinyl alcohol polymer | cellulose derivative | electrolyte | solvent | kind of resin | solvent |
| comparative example 3 | acryl-denaturated polyvinyl (100 %) | — | sodium acetate (0.5 %) | 80% alcohol aqueous solution (100 ml) | ethyl cellulose (2 g) | 100% alcohol aqueous solution (100 ml) |
| sample 7-1 | acryl-denaturated polyvinyl alcohol (65%) | ethyl cellulose (35%) | sodium acetate (0.5%) | 80% alcohol aqueous solution (100 ml) | polybutyl alcohol (2 g) | 100% alcohol aqueous solution (100 ml) |
| sample 7-2 | acryl-denaturated polyvinyl alcohol (55%) | ethyl cellulose (45%) | sodium acetate (0.5%) | 80% alcohol aqueous solution (100 ml) | ethyl cellulose (2 g) | 100% alcohol aqueous solution (100 ml) |
| sample 7-3 | acryl-denaturated polyvinyl alcohol (55%) | ethyl cellulose (35%) | toluenesulfonic acid triethanol amine salt (50%) | 80% alcohol aqueous solution (100 ml) | ethyl cellulose (2 g) | 100% alcohol aqueous solution (100 ml) |
| sample 7-4 | acryl-denaturated polyvinyl alcohol (55%) | ethyl cellulose (45%) | sodium acetate (0.5%) | 80% alcohol aqueous solution (100 ml) | polybutyl alcohol (1 g) ethyl alcohol (1 g) | 100% alcohol aqueous solution (100 ml) |

As is the same with the case of experimental Example 3, the resistance value of each humidity sensitive resistor in each relative humidity was determined. The result obtained is shown in FIG. 9. As is also the same with the case of Example 3, after each humidity sensitive resistor was dipped and allowed to stand for a fixed time, it was pulled up from the water and dried, and the resistance value in 90% relative humidity was determined. This result is shown in FIG. 11.

Figure 11:
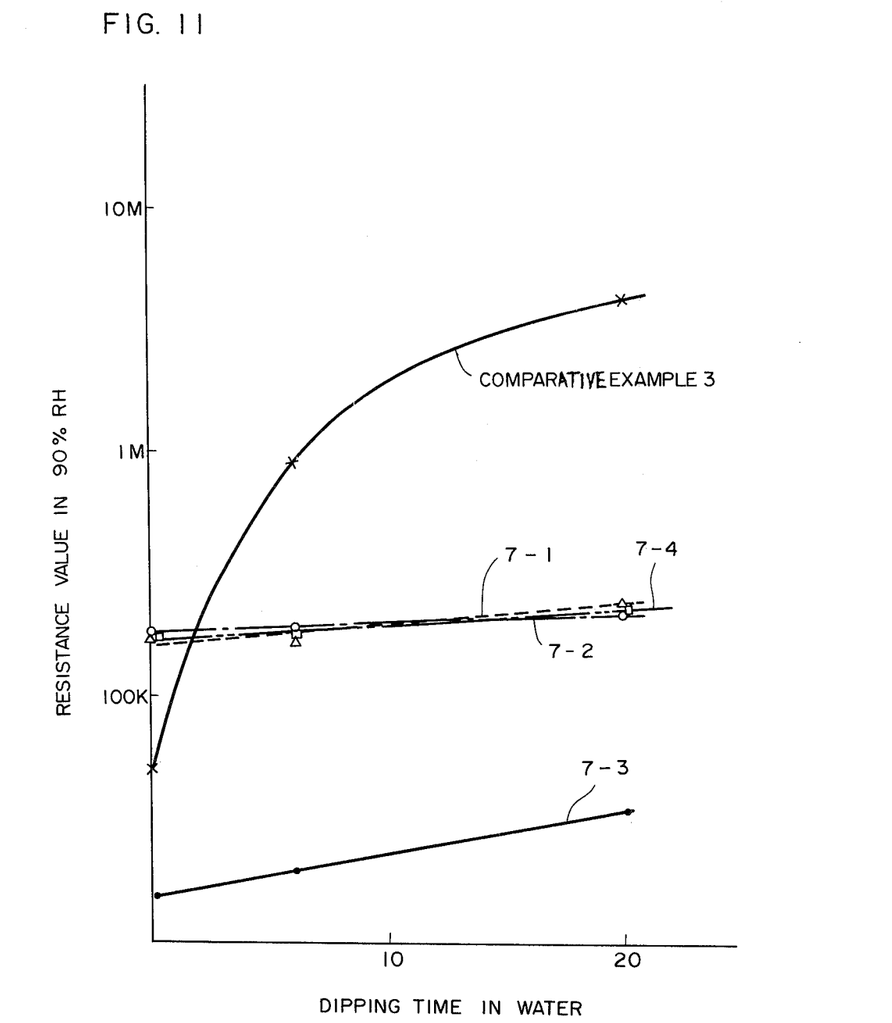
FIG. 11 is a graph showing the resistance value in 90% relative humidity of the experimental Example 2 of the second embodiment.

As is evident from FIG. 11, each humidity sensitive resistor of this experimental Example 4 is proved to have a very excellent water resisting property compared with comparative Example 3 in all cases. Further, it is understandable that sample 7-1, sample 7-2, and sample 7-4 show equal resistance value, while sample 7-3 shows considerably small resistance value compared with these three samples. From the result thus obtained, it can be seen that the characteristic can be controlled over considerable wide range by changing the kind and amount of the electrolyte included in the first layer macromolecular resin film.

Although the present invention has been described and illustrated in detail, it is clearly understood that the same is by way of illustration and example only and is not to be taken by was of limitation, the spirit and scope of the present invention being limited only by the terms of the appended claims.

What is claimed is:

1. A humidity sensitive resistor, comprising:
   a pair of detecting electrodes (2, 3) formed on an insulating substrate (1); and
   a humidity sensitive film (4) formed by coating on the detecting electrodes, said humidity sensitive film being formed of an integrated structure of a first layer macromolecular resin film (5) containing a polyvinyl alcohol polymer and an electrolyte and a second layer of hygroscopic macromolecular resin film (6) coating on said first layer macromolecular resin film (5), said humidity sensitive resistor being characterized in that the water absorbing rate of the second layer high molecular resin film (6) by moisture absorption is smaller than that of the first layer macromolecular resin film (5).

2. A humidity sensitive resistor in accordance with claim 1, wherein said first layer macromolecular resin film (5) further comprises a cellulose derivative.

3. A humidity sensitive resistor in accordance with claim 2, wherein said second layer macromolecular resin film (6) comprises at least one member selected from the group consisting of a polyalkyl alcohol polymer and a cellulose derivative.

* * * * *